United States Patent [19]

Hidy et al.

[11] 3,965,274

[45] June 22, 1976

[54] METHOD OF PREVENTING PREGNANCY WITH LACTONE DERIVATIVES

[75] Inventors: Phil H. Hidy, Terre Haute; Robert S. Baldwin, Montezuma, both of Ind.

[73] Assignee: Commercial Solvents Corporation, Terre Haute, Ind.

[22] Filed: June 7, 1974

[21] Appl. No.: 477,406

Related U.S. Application Data

[63] Continuation of Ser. No. 273,439, July 20, 1972, abandoned, which is a continuation of Ser. No. 28,967, April 15, 1970, abandoned, which is a continuation-in-part of Ser. No. 512,111, Dec. 7, 1965, abandoned.

[52] U.S. Cl. .................................... 424/279
[51] Int. Cl.² ............................. A61K 31/365
[58] Field of Search ........................... 424/279

[56] References Cited
UNITED STATES PATENTS

| | | | |
|---|---|---|---|
| 3,239,341 | 3/1966 | Hodge et al. ............. | 424/279 |
| 3,239,345 | 3/1966 | Hodge et al. ............. | 424/279 |
| 3,239,354 | 3/1966 | Hodge et al. ............. | 424/279 |

OTHER PUBLICATIONS

Goldzieher et al. – Western Journal of Surgery, Obstetrics & Gynecology, vol. 71, (1963) p. 187.

*Primary Examiner*—Sam Rosen
*Attorney, Agent, or Firm*—Morton, Bernard, Brown, Roberts & Sutherland

[57] ABSTRACT

A method for inhibiting pregnancy in female mammals which comprises administering an effective amount of a compound having the formulae:

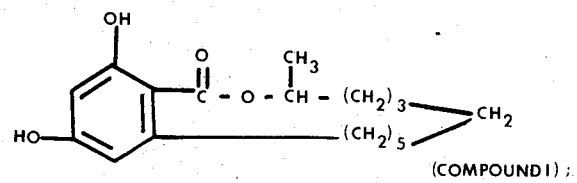

(COMPOUND I);

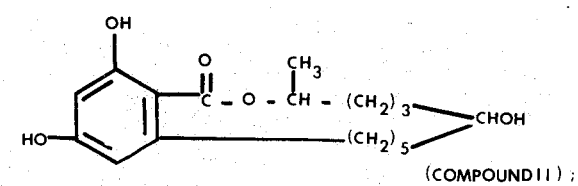

(COMPOUND II);

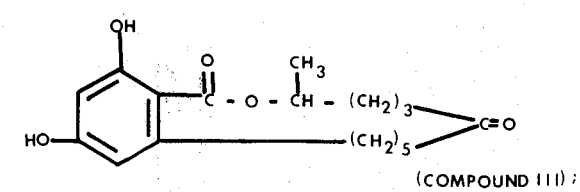

(COMPOUND III);

or

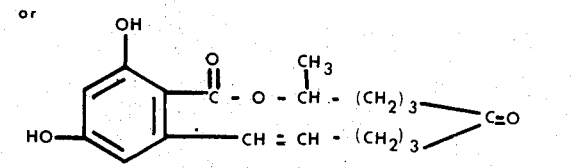

The compound is administered for at least one full estrus cycle to insure prevention of pregnancy and thereafter as long as it is desired.

10 Claims, No Drawings

METHOD OF PREVENTING PREGNANCY WITH LACTONE DERIVATIVES

This application is a continuation of application Ser. No. 273,439, filed July 20, 1972, now abandoned; which in turn is a continuation of application Ser. No. 28,967, filed Apr. 15, 1970, now abandoned; which in turn is a continuation-in-part of application Ser. No. 512,111, filed Dec. 7, 1965, now abandoned.

The present invention is directed to pharmaceutical and veterinary compositions and to their use in preventing pregnancy in female mammals.

In accordance with the present invention, there is provided a pharmaceutical and/or veterinary composition containing as an active ingredient a compound having the structural formulae:

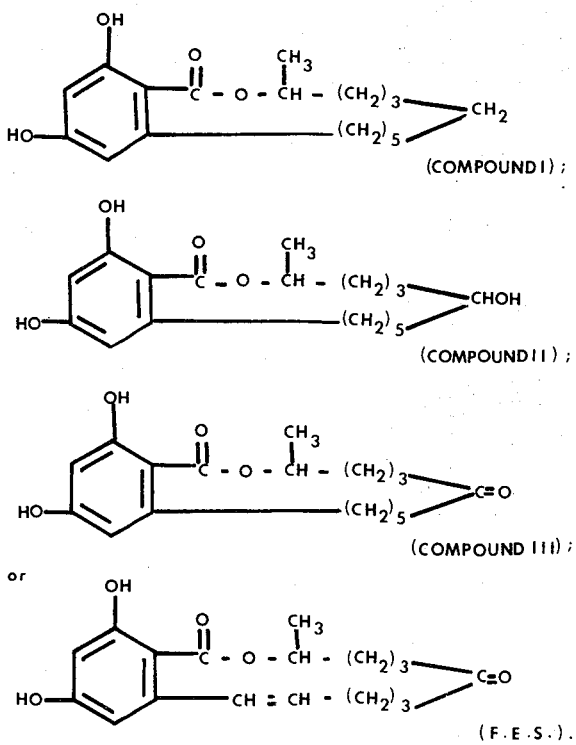

which composition when administered to female mammals prevents pregnancy.

The pharmaceutical and veterinary compositions of the invention can be prepared by mixing the active ingredient with non-toxic, pharmaceutically-acceptable carriers, which ca be inert diluents or solid carriers, and forming the resulting mixture into suitable dosage forms. The compositions can be administered to the subject by any suitable method including oral and parenteral administration. Forms suitable for oral administration include, for example, pressed or coated tablets, capsules or pills, syrups, solutions or suspensions in water or non-toxic organic solvent media such as propylene glycol and glycerol formula, dispersible powders and mixtures with animal foodstuffs. Compositions suitable for parenteral administration are the known pharmaceutical forms for such administration, for example, sterile aqueous suspensions or solutions in oily media. The sterile aqueous suspensions can be formulated in the presence of parenterally acceptable buffers, e.g., sodium citrate, citric acid, and/or preservatives such as phenol and methyl and propyl esters of p-hydroxy benzoic acid. A preferred oily media for preparation of the sterile aqueous solution is peanut oil.

The pharmaceutical and veterinary compositions may also include adjuvants known in the art as desirable or useful as, for example, wetting agents, dispersing agents, suspending agents, lubricating agents, sweetening agents, coloring agents and flavoring agents.

Illustrative of oral compositions for humans are tablets wherein the active ingredient is mixed with inert fillers, e.g., dicalcium phosphate, terra alba or lactose in the presence of disintegrating agents as, for example, maize starch and in the presence of lubricating agents such as magnesium stearate. Examples of suitable aqueous suspensions for oral use are those formulated by incorporating the active ingredient in inert pharmaceutically-acceptable liquid solvent media which can contain, if desired, pharmaceutically acceptable thickening agents such as sodium carboxy-methylcellulose and/or pharmaceutically acceptable sweetening and flavoring agents.

The veterinary compositions for oral use may be in the form of a direct blend of the active ingredient with ordinary feed or it may be in the form of a non-toxic powder such as talc, containing the active ingredient for admixture with a feed.

The actual unit dosage of the active ingredient of the invention will vary depending upon the particular species of female mammal but will in all cases be a unit dosage effective to bring about the desired result. In general the dosage will fall in the range of about 0.01, or 0.015 to 25 mg. of active ingredient per kilogram of body weight, such as about 0.01 to 10 mg., preferably 1, or 2 to 5, or 6 mg. per kilogram of body weight per day. Typical dosages for femal;e humans can range from about 0.75 to 500 mg., preferably about 50 or 100 mg. to 200, or 250, mg. per day. The dosage form may be for a single daily dose or in smaller units for multiple dosage or in larger units for division into single doses.

The active ingredient is administered to the female mammal for a period of time effective to prevent pregnancy and to insure that pregnancy is inhibited for the desired period of time. Each species of mammal has/a particular reproductive cycle, e.g. estrus cycle. For humans, this cycle is on the average about 28.4 days. Accordingly, while the active ingredient of this invention begins to inhibit pregnancy upon its initial administration, to insure that pregnancy is prevented, the active ingredient is administered for one full estrus, or reproductive, cycle so that, for example, already fertile eggs lyse. Also, as is well known from the art of oral contraceptives administered to humans, to avoid undesirable side effects in the female reproductive system, such as collection and hardening of blood, it is desirable that administration of such oral contraceptives not be continuous but be such as to allow menstruation. The active ingredient of this invention is administered to humans on the same schedule as such oral contraceptives, e.g., over a twenty-day to twenty-five day period, normally twenty to twenty-two day period, beginning on the fifth day of the cycle, counting the first day of menstruation as day one. Additionally, it is conventional in oral contraceptives for use with humans to include a progestational agent, such as chlormadinone, to make the patient feel better and assist in providing a full menstrual flow during the rest period, i.e. period the drug is not taken. With lower animals the active ingredient is administered continuously except for monkeys which have a cycle, i.e. 28 days, almost identical to humans and are treated as humans. Accordingly, in general, the active ingredient will be administered to the female mammals for from about 70% to 100% of their estrus or reproductive cycle and particularly during their fertile period.

The compounds employed in the present invention include and can be produced from the compound:

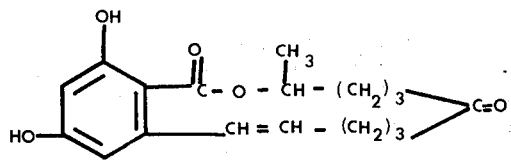

hereinafter referred to as the fermentation estrogenic substance (F.E.S.) by reduction of the ketone group to replace the oxygen of the ketone group with one or two hydrogen atoms and reduction of the olefinic bond. Preparation of the compounds employed in the invention in this manner is described in U.S. Pat. No. 3,239,341, U.S. Pat. No. 3,239,345 and U.S. Pat. No. 3,239,354.

In the production of Compound II having the >CHOH, group, reduction of the ketone group introduces an asymmetric carbon atom and makes diastereoisomers possible. Such isomers include (1) a high melting point isomer, hereafter referred to as "Compound II (HM)", having a melting point of 178°–180°C., and optical activity $[\alpha]_D^{25}$ = about + 46° eq. and, (2) a combination of the THFES(HM) and a low melting point isomer, hereafter referred to as "Compound II (LM)", the combination product having a melting point of 146°–148°C., and optical activity $[\alpha]_D^{25}$ = about + 39° eq., where $[\alpha]$= $\alpha$.100/c.l c = 1% in methanol and 1 = 2 dcm. This product is actually a mixture (about 1:2) of the product melting at 178°–180°C. and its isomer. The low-melting point isomer can be obtained in pure form by crystallization out of the combination product using glacial acid to provide Compound II (LM) which melts at ~155°C. and has optical activity $[\alpha]_D^{25}$ = + 36°.

The reduction of the ketone group can be effected by several procedures including the Clemmensen reduction using zinc and hydrochloric acid; the Wolff-Kishner reduction using hydrazine and alkali, e.g., NaOH, and the formation of the dithioacetal with ethylene dithiol or ethylmercaptan and the catalytic desulfurization of the dithioacetal with Raney nickel catalyst containing adsorbed hydrogen.

The olefinic bond of F.E.S. can be reduced, for example, by hydrogenation in the presence of a Group VIII metal, particularly platinum or palladium, catalyst on a suitable carrier, e.g. charcoal. Generally, the catalyst contains from about 0.01 to about 10% of the catalytic metal. The catalyst is used in a ratio of generally from 0.02 to 2 grams of catalyst, preferably about 0.1 to 0.5 gram, and particularly about 0.2 gram catalyst per gram of F.E.S. The reduction may be carried out while the F.E.S. is dissolved in a suitable solvent, e.g., an alcohol, especially a lower alkanol such as 2-propanol, methanol, ethanol, and acid, e.g., acetic acid, etc., at ambient temperatures; e.g. from about 15° to 40°C., and ambient pressures, since only the presence of hydrogen is required; however, it is preferred to utilize an elevated pressure, e.g. from about 1 to 50 atmospheres of hydrogen. Production of the compound where the ketone group is only partially reduced can be by similar reduction, e.g. in the presence of Raney nickel.

The fermentation estrogenic substance (F.E.S.) from which the compounds of the invention can be prepared is so named since a convenient method for producing it is by cultivating, on a suitable nutrient medium, the organism *Gibberella zeae* (Gordon) on deposit at the Northern Utilization Research and Development Division of the United States Department of Agriculture under the number NRRL-2830. Preparation of the fermentation estrogenic substance is described in detail in U.S. Pat. No. 3,196,019.

The following examples are offered to illustrate this invention but are not to be considered as limiting the invention. The first example illustrates preparation of a suitable inoculum containing the organism *Gibberella zeae* (Gordon) NRRL-2830.

EXAMPLE I

A spore sand culture containing *Gibberella zeae* (Gordon) NRRL-2830 was aseptically placed in a sterile tube containing 15 milliliters of Czapek's-Dox solution and a small amount of agar. This medium was then incubated for about 168 hours at approximately 25°C. At the end of the incubation period, the medium was washed with 5 milliliters of sterile deionized water and transferred to a sterile tube containing 45 milliliters of Czapek's-Dox solution. The contents of the tube was then incubated for about 96 hours at about 25°C. after which the material was available for use in inoculation of a fermentation medium.

The following example illustrates the fermentation of the organism Gibberella zeae (Gordon) NRRL-2830 to produce F.E.S.

EXAMPLE II

To a 2 liter flask were added 300 grams of finely divided corn. The flask and its contents were then sterilized and after sterilization 150 milliliters of sterile deionized water were added. To the mixture in the flask were then added 45 milliliters of the inoculum prepared by the process of Example I and the material was thoroughly mixed. The mixed material was then incubated for about 20 days at 25°C. in a dark room in a water-saturated atmosphere.

The following example illustrates the recovery of F.E.S. from the fermentation medium.

EXAMPLE III

A 300 gram portion of fermented material produced by the method of Example II was placed in 500 milliliters of deionized water and slurried. The slurry was then heated for about 15 minutes at 75°C., 300 grams of filter aid were then added and the material was filtered. The solid filtered material containing the F.E.S. was then air dried, and 333 grams of the dried cake were then extracted with 500 milliliters of ethanol. This procedure was repeated three more times. The ethanol extract was evaporated to dryness under vacuum to give 6.84 grams of solid material. This solid material was then dissolved in 20 milliliters of chloroform and extracted with 30 milliliters of an aqueous solution containing 5% by weight of sodium carbonate having an adjusted pH of about 11.2 The extraction process was repeated seven more times. The pH of the sodium-carbonate extract was then adjusted to 6.2 with hydrochloric acid, to yield a F.E.S.-containing precipitate. The precipitate and the aqueous sodium carbonate extract were then each in turn extracted with 75 milliliters of ethyl ether. This procedure was repeated three more times to yield a light yellow ethereal solution, which was then evaporated to yield 116 milligrams of solid anabolic substance. This material was then subjected to multiple transfer countercurrent distribution using 100 tubes and solvent system consisting of two parts chloroform and two parts carbon tetrachloride as the lower phase and four parts methanol and one part water as the upper phase, all parts by volume. The solid material obtained from the multiple transfer countercurrent distribution was F.E.S.

EXAMPLE IV

Two 10 gram portions of F.E.S. each in 200 milliliters acetic acid, were catalytically reduced at room temperature in the presence of 1.2 grams of PdO catalyst at a hydrogen pressure of about 45 psi. The combined reduction mixtures were heated to boiling, filtered, and the filter cake was washed with 50 milliliters of hot acetic acid. The cooled filtrate was added, with stirring, to 2 liters of water. The mixture was stirred for 15 minutes and the white solid was collected by filtration, washed and dried in a vacuum desiccator to yield 19.1 grams of dihydro F.E.S. having a melting point of 191° – 193°C. The dihydro F.E.S. (1 gram) is added slowly with cooling (ice-bath), to a mixture of 5 cc. of ethylene dithiol, 0.25 .25 gram of freshly fused zinc chloride and 2 grams of anhydrous sodium sulfate, contained in a microflask. The mixture is maintained at 5°C. for 20 hours and then at room temperature for 4 hours, whereupon it is poured into 50 cc. of ice and the precipitate is collected and subjected to hydrogenolysis. To the reaction product is added 100 cc. of 90% ethanol and 15 grams of Raney nickel catalyst and the mixture is refluxed until the reaction is complete. The nickel is removed by centrifugation and is washed several times with hot ethanol by centrifugation followed by decantation, and the centrifugates are combined. The mixture is evaporated to dryness and the residue is suitably recrystallized to yield a compound having the formula:

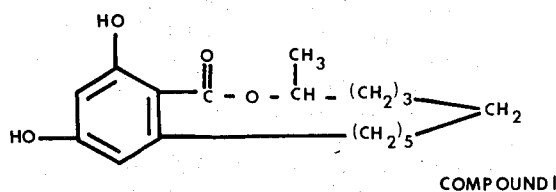

COMPOUND I

EXAMPLE V

Pharmaceutical preparation containing Compound I in the form of tablets suitable for administration to humans is prepared by triturating 246 grams of the compound with 60 grams of lactose to form an homogeneous powder. To the powder is added 20 grams silicic acid with hydrolyzed starch and water and the mixture stirred until a homogeneous paste is formed. The paste is then dried and tabletted with 2 grams magnesium stearate to form tablets containing approximately 150 mg. of active ingredient. F.E.S., compounds II (HM) and II (LM) and Compound III are similarly tabletted. These compounds can be administered to female mammals in daily amounts of 10 and 25 mg. active ingredient per kilogram of body weight to inhibit pregnancy.

EXAMPLE VI

A pharmaceutical preparation of an aqueous suspension for oral administration to inhibit pregnancy in female mammals has the following composition:

Recipe for 1000 ml. of suspension

| | |
|---|---|
| Compound I | 30.0 g. |
| Sucrose | 400.0 g. |
| Powdered tragacanth | 7.5 g. |
| Flavoring essential oil | 0.2 ml. |
| Methyl p-hydroxybenzoate | 2.0 g. |
| Propyl p-hydroxybenzoate | 0.5 g. |
| Glycerol | 150.0 ml. |
| Citric acid | 2.0 g. |
| Benzoic acid | 1.0 g. |
| Distilled water | (to complete 1000 ml.) |

Preparation of this suspension is accomplished by mixing the glycerol, benzoic acid, methyl and propyl benzoic acids, tragacanth gum, flavoring oil and active ingredient into a homogeneous mass. An aqueous solution of the citric acid is then added with slurrying and finally the sucrose is added. Slurrying is continued until a homogeneous suspension is obtained to which is added the balance of the water. Similar compositions are prepared using F.E.S., Compounds II (HM) and (LM) and Compound III, respectively, in place of Compound I.

EXAMPLE VII 100 mg. of Compound I, 0.2 mg. of methyl-p-methoxybenzoate, 0.5 mg of sodium citrate and 0.2 mg. of citric acid are added to 1 ml. of water. The pH of the suspension is adjusted to 5 with HCl. Heat sterilization results in an aqueous suspension suitable for parenteral injection.

EXAMPLE VIII

Mature, non-parous female rats of the Sprague-Dawley strain of similar age and in proestrus on the first day of test were selected for this test. One group of three rats was administered 0.3 mg/day of Compound I and a second group of three rats 1.0 mg/day. Administration was by subcutaneous injection employing sterilized aqueous suspension of the active ingredient in propylene glycol. A third group of five rats was used as a control.

Adult males of the Sprague-Dawley strain of proven fertility were placed in the female's cage and left for a period of 48 hours. Vaginal smears were taken to determine if insemination had occurred. Treatment of the female rats was continued for a total of 7 days. On the eighth day the female rats were not treated and on the ninth day, the female rats were autopsied and the number of implantation sites on the uterus were counted. The results are summarized in the table below wherein the percentage of inseminated rats without implantation sites is recorded as the percentage inhibition of fertility.

| 1 Compound | 3 Daily Dose mg. | 4 Ave. No. of Implant Sites | 5 Number Inseminated |
|---|---|---|---|
| Controls | 0 | 11.6 | 5/5 |
|  | 0.3 | 0 | 3/3 |
| COMPOUND I | 1.0 | 0 | 3/3 |
|  | 6 | 7 |  |
| Compound | Number Pregnant |  | Percent Inhibition |
| Controls | 5/5 |  | 0 |
|  | 0/3 |  | 100 |
| COMPOUND I | 0/3 |  | 100 |

The data of the table demonstrates that the compound of the invention was 100% effective in preventing pregnancy in the rats tested.

EXAMPLE IX

The results presented below indicate that Compound II interferes with pregnancy by inhibition of pituitary support of the ovary, increased rate of transport of blastocysts along the reproductive tract and by depression of inhibition of placental function.

One possible mechanism whereby antifertility agents can exert their effect is by increasing or delaying, normal transport mechanisms of blastocysts. Normally in rats, blastocysts are found in the upper third of the oviduct when inspected 24 hours after ovulation, in the middle portion at 36 hours and in the lower third of the oviduct by 48 hours.

Compound II (HM) was administered to groups of inseminated females 8 hours, 12 hours or 12 and 36 hours following ovulation. Compounds were administered subcutaneously in CMC. Animals were killed and the oviducts flushed 24 hours after the last treatment.

Compound II (HM), at the doses used, did not affect the numbers or location of the blastocysts when administered 8 hours after ovulation. When injected on the first day (12 hours after ovulation) 120 and 180 $\mu$g. of Compound II (HM) resulted in marked decreases in the numbers of blastocysts recovered. Treatment with 180 $\mu$g. of Compound II (HM) on days 1 and 2 of pregnancy produced loss of all blastocysts from the reproductive tract. The data obtained support the view that Compound II (HM) acts to increase the rate of passage of blastocysts through the oviducts. This confirms the response noted where the compound inhibited implantation by this mechanism.

Compound II (HM) was administered on the day of insemination and 24 and 48 hours later. The uteri and oviducts were flushed on the day after the last injection for the presence of blastocysts. When found, their location was recorded. In the control group most of the blastocysts had just entered the upper end of the uterus; a few (5) remained in the oviducts. A total loss of blastocysts from the reproductive tract was obtained in the group treated with 120 $\mu$g. Compound II (HM) and 60 $\mu$g. was sufficient to move most of the blastocysts to the lower portion of the tract.

To determine any direct effects of Compound II (HM) on the blastocysts the compound was administered in daily subcutaneous injections for the first 4 days of pregnancy in rats. On the 5th day these "donor" rats were killed and the "treated" blastocysts were flushed from the uteri and transferred to the uteri of recipient, pseudopregnant rats (4th day of pseudopregnancy). These animals were killed on the 13th day of pseudopregnancy and the uteri were inspected for implantation sites. Non-treated recipient rats contained implants in 5/6 of the animals; 21 of 60 transferred blastocysts were implanted. Compound II at doses of 100 and 200 $\mu$g. per day did not affect the ability of the transferred blastocysts to implant in the recipient rats. This would indicate that the antifertility effects of this compound, noted in other experiments was not mediated by a direct blastocidal means.

The estrogenic potency of Compound II (HM) was sufficiently great to cause inhibition of pregnancy when administered during the first 7 days of gestation. Unlike natural estrogens, Compound II (HM) failed to stimulate implantation of blastocysts in pregnant rats where implantation was delayed by ovariectomy and progesterone treatment. In these "delayed" animals, as well as in animals where transport of embryos was studied, Compound II (HM) caused accelerated movement of the blastocysts along the reproductive tract.

Evidence was presented indicating that lysis of the embryos could also result from treatment with Compound II (HM). Compound II (HM) did not produce any detrimental effect on the embryos when the compound was administered during the first four days of pregnancy. Blastocysts recovered from these animals and transferred to recipient pseudopregnant rats did not differ from control values. The doses used were effective as inhibitors of pregnancy if administered over longer periods of time. Compound II (HM) was effective in inhibiting the decidual response in pseudopregnant rats. Thus, whether directly or indirectly, the compound appears able to interfere with placental function.

EXAMPLE X

Five sows that had farrowed three normal litters prior to treatment were observed three months to establish their estrus cycle and thereafter were treated at various time intervals following establishment of the estrus cycle in dosages of 50, 100 and 150 mg./day/sow of F.E.S. for periods ranging between 34 and 56 days. Oral treatment with F.E.S. at 100 and 150 mg. daily, beginning day ten of the estrus cycle, and continuing for 35 days effected a suspension of estrus for 96 to 104 days after treatment was withdrawn. Under a similar treatment, 50 mg./day did not prevent estrus on the 20th day and continued administration prevented estrus until 105 days after withdrawal. Daily administration of 150 mg. starting on day 14 failed to prevent estrus on day 20. Treatment was withdrawn at 56 days. Estrus did not become evident until 139 days after withdrawal. One sow which received 150 mg. F.E.S. on day 12 and through day 70 (56 days treatment) failed to return to estrus 200 days after treatment was withdrawn. This series of observations demonstrates that F.E.S. is effective in interrupting the estrual cycle of sows, for instance starting day 10 and treating 30 to 35 days with doses of 50 to 100 mg./day/sow was effective.

period of 270 days. The last five days of each 22 day period the patients were also provided 2 mg. chlormadinone. Table I sets forth the results.

TABLE I

| Patient | Age | Children | Day | Biopsy | Remarks |
|---|---|---|---|---|---|
| 69-A | 27 | 3 | 0 | Secretory endometrium (cf. 24th d. of cycle) | From 7th to 9th cycle — no complaints, cycles regular, Pregnandiol 0.6 mg. No complaints. (20 days treatment, last 5 days include 2 mg. chlormadinone). Normal or abundant withdrawal bleeding monthly. |
| LMP 5-10* | | | 22 | Late prolif. endom. Moderate mitotic activity. | |
| On Drug 5-15 Prev. Delivery, 6 mo. | | | 180 | Late prolif. endom. Good mitotic activity. | |
| 70-A | 22 | 4 | 0 | Late secretory endom. (cf. 23rd d. of cycle). | 22nd day — No complaints — Primolut 4 days after completion — normal menses 3 d. later at 180 d. Schedule 20 d. treatment, last 5 days include 2 mg. chlormadinone. Normal withdrawal bleeding every month — no complaints. No complaints 7th to 9th cycle. On 8th cycle flow abundant and lasted 7 days. Pregnandiol 0.9 mg. |
| LMP 4-21* | | | 22 | Late prolif. endom. with slight mitotic activity. | |
| On Drug 4-26 Prev. Delivery, 3 mo. | | | 180 | Late prolif. endom. Pregnandiol 0.9 mg. | |
| 71-A | 34 | 9 | 0 | Late secretory endom. (cf. 24th d. of cycle). | 22nd — Slight mucorrhea first days of treatment. Moderate withdrawal bleeding after stopping drug. 180 d. schedule — same as 70-A. Scarce withdrawal bleeding every month. Slight mucorrhea 1st two cycles; nervousness 4th cycle. No complaints and cycles regular. |
| LMP 4-13* | | | 22 | Intermed. prolif. endom. Slight mitotic activity. | |
| On Drug 4-18 Prev. Delivery, 5 mo. | | | 180 | Intermed. prolif. endom. Pregnandiol 0.4 mg. | |
| 72-A | 30 | 6 | 0 | Secretory endometrium (cf. 21st d. of cycle). | 22nd — No complaint. Received Primolut and menstruated 3 days later. 180 d — Slight irregularity of cycle despite fact same schedule as 71-A. In 7th and 8th cycles delays of 5 to 6 days of start of menstrual flow. In 9th cycle became pregnant. Pregnandiol 0.9 mg. |
| LMP 4-22* | | | 22 | Late prolif. endom. with patchy hyperplasia. | |
| On Drug 4-27 Prev. Delivery, 3 mo. | | | | | |
| 73-A | 23 | 2 | 0 | Secretory endometrium (cf. 19th day of cycle). | 22nd — Slight nausea first days. Abundant flow 4 days after stopping drug. 180 d — schedule same as 70-A. No complaints — periods regular and flow moderate. No complaints. From 7th to 9th cycle periods regular and normal. Pregnandiol 0.4 mg. |
| LMP 5-1* | | | 22 | Late prolif. endom. Good mitotic activity. Pregnandiol 0.6 mg. | |
| On Drug 5-5 Prev. Delivery, 6 mo. | | | | | |
| 74-A | 27 | 4 | 0 | Secretory Endometreium with unevenly developed glands. | 22nd — No complaints — carrier of amoeba histolytica. Primolut on 6 d. — menses 4 days later. 180 d. — No complaints — Periods regular and flow moderate. Schedule — same as 70-A. No complaints. From 7th to 9th cycle periods regular and flow normal. Pregnandiol 0.7 mg. |
| LMP 5-4 | | | 22 | Intermed. prolif. endom. Slight mitotic activity. Pregnandiol 0.7 mg. | |
| On Drug 5-9 Prev. Delivery, 3 mo. | | | 180 | Late prolif. endom. Good mitotic activity. Pregnandiol 0.4 mg. | |
| 75-A | 25 | 3 | 0 | Premenstrual secretory endom. (cf. 27th day). | Patient used contraceptive coil until 3/67. No complaints — abundant bleeding 4 days after stopping drug. Same schedule as 70-A. Breakthrough bleeding for 3 days in 3rd cycle. Periods regular; flow moderate or abundant. Slight pre-menstrual headache before 8th cycle. No problems 7th and 9th cycles. Flow and cycle normal. Pregnandiol 0.6 mg. |
| LMP 4-17 | | | 22 | Late prolif. endom. with min. mitotic activity. Pregnandiol 0.5 mg. | |
| On Drug 4-22 Prev. Delivery, 1 year | | | 180 | Late prolif. endom. Patchy hyperplasia. Pregnandiol 0.3 mg. | |
| 76-A | 31 | 7 | 0 | Secretory endometrium (cf. 22nd day of cycle). | Slight mucorrhea last day of treatment. Five days after treatment got Primolut; normal period in 3 days. Same schedule as 69-A. Periods regular, flow slight to moderate. Mucorrhea in 2nd and 3rd cycles; slight nausea second cycle. 7th and 8th cycles no complications. 9th cycle breakthrough bleeding on days 13 and 14 and 5. Flow normal. Pregnandiol 1.1 mg. |
| LMP 5-11* | | | 22 | Intermed. prolif. endom. Poor mitotic activity. Pregnandiol 0.9 mg. | |
| On Drug 5-16 Prev. Delivery, 4 mo. | | | 180 | Late prolif. endom. Patchy hyperplasia. Pregnandiol 0.3 mg. | |
| 77-A | 29 | 4 | 0 | Secretory endometrium (cf. 23rd day of cycle). | No complaints — Spntaneous bleeding 3 days after stopping drug. Schedule same as 69-A. Breakthrough bleeding 4 days in second cycle. Periods regular and flow abundant. No complaints. From 7th to 9th cycle and flow normal. |
| LMP 5-7 | | | 21 | Late prolif. endom. Good mitotic activity. Pregnandiol 0.6 mg. | |
| On Drug 5-12 Prev. Delivery, 5 mo. | | | 180 | Intermed. prolif. endom. Slight mitotic activity. Pregnandiol 1.7 mg. | |
| 78-A | 36 | 5 | 0 | none. | No complaints. Got Primolut and had abundant flow 4 days later. Same schedule as 71-A. |
| LMP 4-30 | | | 22 | Late prolif. endom. Good mitotic activity. Pregnandiol 0.9 mg. | Period regular and flow moderate. Treatment interrupted because went to live in another town. No problems on 7th and 8th cycles. |
| On Drug 5-4 Prev. Delivery, 4 mo. | | | 180 | Early prolif. endom. Good mitotic activity. Pregnandiol 0.6 mg. | |

*LMP = LAST MENSTRUAL PERIOD — Month/day

EXAMPLE XI

Human female patients were given orally 100 mg./day of Compound II (HM) for 22 day periods beginning with the 5th day of each menstruation cycle, the first day of menstruation being day one, for a total The contraceptive results were very good with the exception of Patient 72-A who became pregnant in the 9th cycle; however, there was some question regarding the patient's adherence to the schedule. All patients menstruated regularly and breakthrough bleeding was not abnormal in frequency. Compound II (HM) was an effective oral contraceptive.

EXAMPLE XII

Human female patients were administered F.E.S. for 60 days at dosages of 100 mg./day and 200 mg./day on the same schedule as Example XI where for days 5 through 17 the drug is administered, days 18 to 22 the drug plus 2 mg. chlormadinone are administered and then the patient rests until day 5. Table II sets forth data at 200 mg./day/patient and Table III sets forth data at 100 mg./day/patient. F.E.S. is an effective contraceptive.

TABLE II

| Patient | Age | Children | Day | Vaginal Cytology | Remarks |
|---|---|---|---|---|---|
| 129-A Prev. Delivery 3 mo. | 29 | 5 | 0 | Secretory endometrium. cf. 20th day of cycle. | Slight nausea first day of first treatment cycle. Periods normal. |
| 130-A Prev. Delivery 6 mo. | 23 | 3 | 0 | Late secretory endometrium cf. 26th day of cycle. | No problems. First cycle flow heavier than usual; in second infrequent mucorrhea. |
| 131-A Prev. Delivery 4 mo. | 32 | 7 | 0 | Late secretory endom. cf. 24th day of cycle. | No problems. Cycles regular and flow normal. |
| | | | 21 | Early secretory endom. cf. 18th day of cycle. | |
| 132-A Prev. Delivery 6 mo. | 25 | 2 | 0 | Not done. | No general problems. Slight mucorrhea at end of first cycle. Cycle normal and flow slightly increased. |
| | | | 21 | Late prolif. endom. moderate mitotic activity. | |
| 133-A Prev. Delivery 6 mo. | 34 | 7 | 0 | Late secretory endom. cf. 24 day of cycle. | No general problems. In first normal cycle her menstrual period normal. In second cycle pregnancy proved after 13 days. |
| | | | 20 | Late secretory endom. cf. 23rd day of cycle. | |
| 134-A Prev. Delivery 3 mo. | 26 | 4 | 0 | Late secretory endom. cf. 27th day of cycle. | Patient felt well. Cycle and period normal. |
| | | | 22 | Late prolif. endom. moderate mitotic activity. | |
| 135-A Prev. Delivery 7 mo. | 35 | 8 | 0 | Secretory endometrium. cf. 10th day of cycle. | No general problems. In first cycle flow low. In second cycle flow normal. |
| | | | 21 | Intermed. prolif. endom. moderate mitotic activity. | |
| 136-A Prev. Delivery 5 mo. | 30 | 6 | 0 | Secretory endometrium. cf. 22nd day of cycle. | No general problems. Periods and flows normal in both cycles. |
| | | | 10 | Secretory endometrium. cf. 20th day of cycle. | |
| 137-A Prev. Delivery 4 mo. | 23 | 1 | 0 | Secretory endometrium. cf. 24th day of cycle. | No general problems. First cycle normal. In second cycle delay of 5 days of onset of flow. |
| | | | 20 | Late prolif. endom. moderate mitotic activity. | |
| 138-A Prev. Delivery 8 mo. | 35 | 9 | 0 | Secretory endometrium. cf. 20th day of cycle. | Patient felt well. Both cycles normal. |
| | | | 22 | Late prolif. Endom. good mitotic activity. | |

TABLE III

| Patient | Age | Children | Remarks |
|---|---|---|---|
| 109-A Prev. Delivery 3 mo. | 26 | 6 | No complaints. Treatment stopped after 3 cycles. Control cycle biopsy - late secretory endometrium like that seen 22nd day of cycle. |
| 110-A Prev. Delivery 10 mo. | 33 | 7 | No complaints. First cycle normal flow; second cycle no menses; pregnant in third cycle. Claims did not omit any pills. Control cycle biopsy - late secretory endometrium (cf. 25th day). |
| 111-A Prev. Delivery 5 mo. | 25 | 3 | Slight nausea first days of first cycle. No other complaints. Stopped treatment after 3 cycles. Control cycle biopsy - early secretory endometrium (like 18th day). |
| 112-A Prev. Delivery 7 mo. | 30 | 6 | No complaints. Discontinued after 3 cycles. Control cycle biopsy - late secretory endometrium (cf. 26th day of cycle). |
| 113-A Prev. Delivery 11 mo. | 34 | 7 | No major complaints; in second cycle 3 or 4 days moderate headache. Endometrical biopsy after 18 days of drug - late proliferative endometrium, good mitotic activity. Control cycle biopsy - early secretory endometrium (cf. 17th day of cycle). |
| 114-A Prev. Delivery 4 mo. | 20 | 1 | No complaints. No flow at end of first cycle, but took pills until pregnant. Probably did not take 3 or 4 pills on first cycle. Control cycle biopsy - late secretory endometrium (cf. 25th day of cycle). |
| 115-A Prev. Delivery 5 mo. | 29 | 5 | Slight nausea at start of first cycle. Periods regular and flow abundant. Control cycle biopsy - intermediate proliferative endometrium with mod. mitotic activity. |
| 116-A Prev. Delivery 11 mo. | 36 | 7 | No complaints. First cycle low flow; did not menstruate second cycle; third cycle pregnancy. Control cycle biopsy - late secretory endometrium (cf. 27th day of cycle). |
| 117-A Prev. Delivery 4 mo. | 22 | 2 | No complaints. Menses regular and flow moderate. Endometrial biopsy after 18 days of drug - secretory endometrium of 20th day of cycle. Control cycle biopsy - late secretory endometrium (cf. 24th day of cycle). |
| 118-A | 35 | 9 | No complaints. Period slightly prolonged; flow moder- |

TABLE III-continued

| Patient | Age | Children | Remarks |
|---|---|---|---|
| Prev. Delivery 8 mo. | | | ate to abundant. Control cycle biopsy - secretory endometrium (cf. 19th day of cycle). |

These results demonstrate the anti-ovulatory function of F.E.S. On the regime used there were no adverse reactions and good estrogenic response as indicated by vaginal cytology.

EXAMPLE XIII

Groups I, II, III and IV each composed of human female patients were given orally 10, 25, 50 and 100 mgs/day, respectively, of pure Compound II (LM) having a melting point of about 155°C. for 22 day periods beginning with the 5th day of each menstruation cycle, the first day of menstruation being day one, for a total period of 90 days. The last five days of each 22 day period the patients were also provided 2 mg. chlormadinone. The results were as follows:

| Group | Dose | Results at 90 days[1] |
|---|---|---|
| I | 10 | 3 per 10 |
| II | 25 | 2 per 8 |
| III | 50 | 2 per 12 |
| IV | 100 | 0 per 10 |

[1]number of pregnancies per total number treated

The pure compound II (LM) can be separated from a mixture of it and its high melting diastereoisomer by solubilizing the mixture in glacial acetic acid and crystallizing out the pure compound II (LM) in accordance with the process described in the copending patent application of Vernon V. Young, Ser. No. 643,819 filed June 6, 1967, now U.S. Pat. No. 3,574,235, herein incorporated by reference.

It is claimed:
1. A method of preventing pregnancy in female humans experiencing a reproductive cycle which comprises administering to said female human in unit dosage form an effective amount to prevent pregnancy of a compound of the formula selected from the group consisting of:

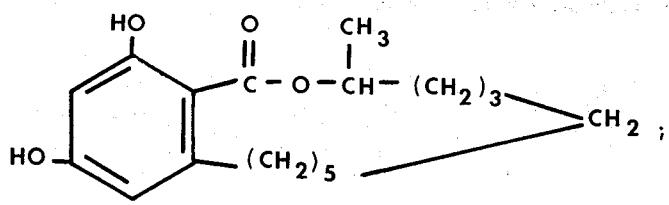

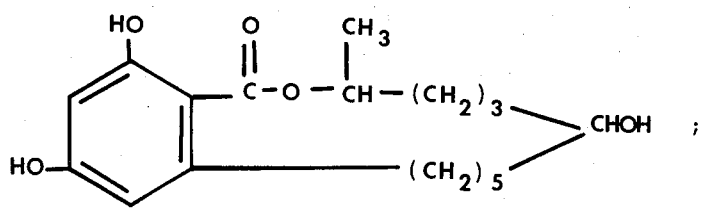

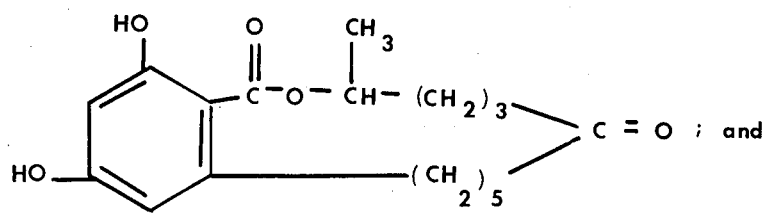

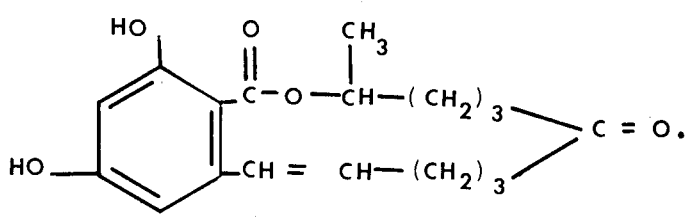

2. The method of claim 1 wherein the compound is administered for a time effective to prevent pregnancy and the dosage of the compound is about 0.01 to 10 mg. per kilogram of body weight per day.

3. The method of claim 2 wherein the compound is administered during a reproductive cycle for 20 to 25 days beginning on the fifth day after the first day of menstruation.

4. The method of claim 2 wherein the compound is administered orally.

5. The method of claim 4 wherein the compound is administered in the amount of about 50 to 250 mg. per day.

6. The method of claim 2 wherein the compound is administered for from about 70 to 100% of the reproductive period including the fertile period.

7. The method of claim 2 wherein the compound is

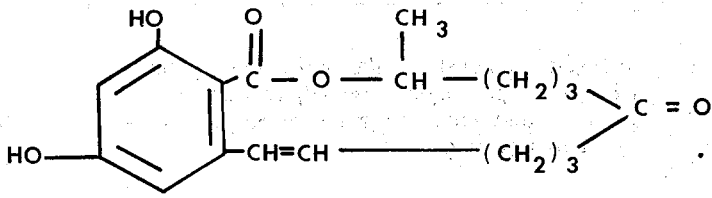

8. The method of claim 2 wherein the compound is

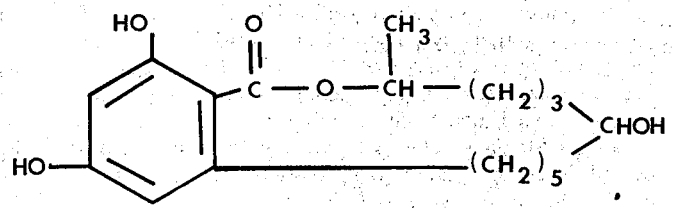

9. The method of claim 8 wherein the compound is the low melting diastereoisomer having a melting point of about 155°C.

10. The method of claim 8 wherein the compound is the high melting diastereoisomer having a melting point of 178°–180°C.

* * * * *